(12) United States Patent
Borden et al.

(10) Patent No.: US 7,901,395 B2
(45) Date of Patent: Mar. 8, 2011

(54) CATHETER HAVING STAGGERED LUMENS AND METHOD

(76) Inventors: Jonathan R. Borden, Sandy, UT (US); Daniel H. Todd, West Highland, UT (US)

(*) Notice: Subject to any disclaimer, the term of this patent is extended or adjusted under 35 U.S.C. 154(b) by 96 days.

(21) Appl. No.: 11/205,000

(22) Filed: Aug. 16, 2005

(65) Prior Publication Data
US 2007/0078437 A1 Apr. 5, 2007

(51) Int. Cl.
*A61M 25/00* (2006.01)
*A61M 31/00* (2006.01)
(52) U.S. Cl. .......................... 604/523; 604/284; 604/508
(58) Field of Classification Search .................. 604/523, 604/284, 508, 264
See application file for complete search history.

(56) References Cited

U.S. PATENT DOCUMENTS

| | | | |
|---|---|---|---|
| 4,619,643 A | 10/1986 | Bai | |
| 5,492,532 A * | 2/1996 | Ryan et al. | 604/103.09 |
| 5,961,485 A * | 10/1999 | Martin | 604/43 |
| 6,270,489 B1 | 8/2001 | Wise et al. | |
| 6,464,686 B1 * | 10/2002 | O'Hara et al. | 604/539 |
| 6,494,875 B1 * | 12/2002 | Mauch | 604/509 |
| 6,511,471 B2 * | 1/2003 | Rosenman et al. | 604/528 |
| 6,537,266 B1 * | 3/2003 | Mottola et al. | 604/523 |
| 6,544,219 B2 * | 4/2003 | Happ et al. | 604/96.01 |
| 6,638,242 B2 * | 10/2003 | Wilson et al. | 604/43 |
| 6,695,832 B2 * | 2/2004 | Schon et al. | 604/544 |
| 6,746,442 B2 * | 6/2004 | Agro et al. | 604/523 |
| 6,758,836 B2 * | 7/2004 | Zawacki | 604/284 |
| 6,916,313 B2 * | 7/2005 | Cunningham | 604/533 |
| 6,921,391 B1 * | 7/2005 | Barker et al. | 604/284 |
| 6,969,381 B2 * | 11/2005 | Voorhees | 604/534 |
| 7,011,645 B2 * | 3/2006 | McGuckin et al. | 604/34 |
| 7,201,745 B2 * | 4/2007 | DiMatteo et al. | 604/523 |
| 2001/0012927 A1 * | 8/2001 | Mauch | 604/284 |
| 2002/0077606 A1 * | 6/2002 | Trotta | 604/264 |
| 2002/0082584 A1 * | 6/2002 | Rosenman et al. | 604/523 |
| 2003/0135199 A1 * | 7/2003 | Rosenman et al. | 604/528 |

(Continued)

FOREIGN PATENT DOCUMENTS

EP 0 495 263 A1 7/1992

(Continued)

OTHER PUBLICATIONS

"Morpheus CT," Angio Dynamics, pp. 1-6, Copyright 2004.

(Continued)

*Primary Examiner* — Kevin C Sirmons
*Assistant Examiner* — Michael J Anderson
(74) *Attorney, Agent, or Firm* — Kirton & McConkie; Craig Metcalf; Mony Ghose

(57) ABSTRACT

A catheter may include a multiple lumen catheter tube, a hub attached to the catheter tube, and a first extension leg and a second extension leg attached to the hub. The multiple lumen catheter tube may include a longitudinal axis, an end, a first lumen, and a second lumen. The first lumen and the second lumen extend through the catheter tube along the longitudinal axis and each having an opening. The end of the catheter tube and the openings of the lumen may be disposed within the hub so that the opening of the first lumen is axially spaced with the end of the catheter tube. The first extension leg may be coupled to the first lumen and the second extension leg may be coupled to the second lumen for the separate delivery of fluids to the lumens.

26 Claims, 9 Drawing Sheets

U.S. PATENT DOCUMENTS

| | | | |
|---|---|---|---|
| 2004/0097903 A1* | 5/2004 | Raulerson | 604/523 |
| 2004/0116901 A1 | 6/2004 | Appling | |
| 2004/0171997 A1* | 9/2004 | Wilson et al. | 604/284 |
| 2004/0176739 A1* | 9/2004 | Stephens et al. | 604/523 |
| 2004/0186444 A1 | 9/2004 | Daly et al. | |
| 2004/0210187 A1* | 10/2004 | Zawacki | 604/43 |
| 2004/0230177 A1* | 11/2004 | DiMatteo et al. | 604/523 |
| 2004/0267213 A1* | 12/2004 | Knapp | 604/284 |
| 2005/0055012 A1* | 3/2005 | Trerotola | 604/508 |
| 2005/0070878 A1* | 3/2005 | Triplett et al. | 604/523 |
| 2005/0080398 A1* | 4/2005 | Markel et al. | 604/508 |
| 2005/0085765 A1 | 4/2005 | Voorhees | |
| 2005/0209581 A1* | 9/2005 | Butts et al. | 604/523 |
| 2005/0209583 A1* | 9/2005 | Powers et al. | 604/533 |
| 2006/0276773 A1* | 12/2006 | Wilson et al. | 604/523 |

FOREIGN PATENT DOCUMENTS

| | | |
|---|---|---|
| WO | WO9907301 | 2/1999 |
| WO | WO9922800 | 5/1999 |
| WO | WO2005025661 A2 | 3/2005 |
| WO | WO2005035022 A2 | 4/2005 |

OTHER PUBLICATIONS

"Maximal Flow Rates Possible During Power Injection Through currently Available PICCs: An In Vitro Study," Ari I. Salis, MD et al., pp. 275-281, Mar. 2004.

"Power Injection of Peripherally Inserted Central Catheters," S. Mitchell Rivitz, Md et al., JVAD, pp. 26-31, Spring 1998.

* cited by examiner

CATHETER HAVING STAGGERED LUMENS AND METHOD

BACKGROUND OF THE INVENTION

The present invention relates to venous access catheters. More specifically, the present invention relates to a multiple lumen catheter for improved resistance to cross lumen leakage at the hub and a method for making a catheter that provides improved resistance to cross lumen leakage at the hub. For example, a multiple lumen catheter according to the invention may be a peripherally inserted central catheter (PICC) or any other type of multiple lumen catheter known in the art.

A PICC is one type of catheter that may be used for the high pressure delivery of intravenous fluids. Previously, PICCs have been used for the low pressure delivery of intravenous fluids and medications. More recently it has become desirable to use a PICC for the administration of contrast agents during diagnostic Computer Tomography (CT) procedures and other radiographic procedures.

A PICC is a catheter that may be inserted in a peripheral location, such as the arm of a patient, with the tip of the PICC positioned above the heart in the superior vena cava. A PICC is intended for long term vascular access and may be designed to remain positioned within a patient for a period ranging from one week to a year. Of course, the period of time that a PICC remains within a patient is dependent on the medicinal regimen administered to the patient through the PICC. Because a PICC is designed for long term use in a patient, a PICC provides a convenient and comfortable means for the administration of medications and may be used in a wide variety of medical settings. For example, a PICC may be used with cancer patients undergoing long term therapy or during a high risk pregnancy where a constant infusion of medications and fluids may be required.

PICCs typically range from about 26 to about 16 gauge sizes. Fluid delivery rates range from about 26-30 cubic centimeters (cc) per hour for a 26 gauge PICC, to over a 1,000 cc per hour for a 16 gauge PICC. Typically, low pressure is used to administer fluids through PICCs at these rates. In comparison, CT procedures usually have an infusion rate of about 4 to 5 cc per second. Additionally, a thicker, more viscous fluid is used in CT procedures. Thus, the pressures involved in CT procedures are much higher.

The majority of currently available PICCs are only able to safely function at pressures less than 100 pounds per square inch (psi) and thus, are unable to meet the demands of high pressure applications where the pressures may reach and exceed 300 psi. Therefore, if a low pressure PICC has been used, a physician must access the patient's vein in another location using a short IV-type needle or catheter designed to withstand higher pressures. However, patients having an inserted PICC are often very ill and gaining access to a vein in another location may be difficult. More specifically, as veins are accessed over time, veins may become inaccessible through damage and scar tissue.

In addition to these low pressure PICCs, high pressure PICCs have been developed. When these currently available high pressure PICCs are used at high pressure, however the PICCs may develop cross-lumen leakage. This can be a serious problem because some medications that are simultaneously administered to a patient through a multiple lumen catheter may form a precipitate if mixed. The precipitate may partially or completely block the PICC, resulting in an unknown quantity of medication being administered to the patient. Alternatively, some medications if mixed prior to being dispersed through the blood stream may be extremely toxic and harmful to the patient.

Additionally, high pressure PICCs are expensive to manufacture. For example, currently available high pressure PICCs may use a titanium or steel hub that is inserted into an end of the catheter tubing. Plastic may then be molded over the metal hub and the end of the catheter tubing in an injection molding process.

The metal hub has several short comings. The metal hub must be machined to relatively tight tolerances and the metal itself may react to the medications being administered, which may limit its usefulness. Additionally, the metal hub complicates disposal of the catheter because it may need to be disposed of separately from the plastic portion of the catheter.

Another short coming of the prior art is that the catheter may still develop cross-lumen leakage at the interface between the metal hub and the catheter tubing. This is because of the radial stresses induced into each lumen of the catheter tubing by the fittings of the metal hub. In addition, low pressure PICCs made entirely of plastic may suffer from cross-lumen leakage at pressures as low as 40 psi.

Low pressure PICCS known in the art may be formed by cutting a multiple lumen catheter tube to size, inserting a mandrel into each lumen of the catheter, and molding a hub over the mandrels and the end of the multiple lumen catheter tube. Lastly, the mandrels are removed from the hub and extension legs attached to the hub to complete the catheter. A short coming of this type of catheter is that the multiple lumen catheter tube is cut flush so that the mandrels are positioned side by side in the end of the multiple lumen catheter tube which may stress and stretch the inner wall of the multiple lumen catheter tube. This stress and stretch of the inner wall of the multiple lumen catheter tube can result of cross-lumen leakage even under relatively low pressures, such as 40 psi.

Another shortcoming that can affect the performance of multiple lumen catheters is the formation of plastic flaps in the lumens of the catheter during the manufacturing process. As the hub is molded over the end of the multiple lumen catheter tube, the molding process may spread the mandrels allowing small fingers of plastic to flow into the lumens. Often these fingers of plastic have cooled enough that they fail to fully adhere to the multiple lumen catheter tube. Thus, these fingers of plastic may act as flaps that may potentially reduce the flow of liquids through that lumen of the catheter or may become dislodged and potentially flow into a patient.

Therefore, a need exists for a catheter that may be made entirely of plastic to facilitate the disposal and recycling of used catheters. A need exists for a hub that minimizes the radial stresses in the multiple lumen catheter tubing to increase the catheter's resistance to cross-lumen leakage. Additionally, a need exists for a method of manufacturing a catheter that resists the formation of flaps within the lumen of the catheter.

BRIEF SUMMARY OF THE INVENTION

The apparatus of the present invention has been developed in response to the present state of the art, and in particular, in response to the problems and needs in the art that have not yet been fully solved by currently available catheters and more specifically PICCs. Thus, the present invention provides a multiple lumen catheter for use in the high pressure administration of liquids that increases the catheters resistance to cross lumen leakage at the hub.

In accordance with the invention as embodied and broadly described herein in the preferred embodiment, a multiple lumen catheter for use in high pressure applications that may be made entirely of plastic is provided. According to one embodiment, the catheter includes a means for preventing cross-lumen leakage, such as a hub, and a catheter tube comprising a longitudinal axis, a first lumen, and a second lumen. The first lumen and the second lumen of the catheter tube extend through the catheter tube along the longitudinal axis, which may be the center line of the catheter tube.

The first lumen and the second lumen each have an opening that is axially spaced from the other. Thus, when the lumens of the multiple lumen catheter tube are aligned along the longitudinal axis, the opening of the first lumen is axially spaced from the opening of the second lumen. In other words, the openings of the lumens are staggered along the longitudinal axis. By spacing the openings of the first lumen and the second lumen, the radial stresses induced into the catheter tubing during the attachment of the hub are reduced. In some configurations, the hub of the catheter may be attached to the catheter tube so that the opening of the first lumen and the opening of the second lumen are disposed within the hub. In some configurations, an end of the catheter tube may be disposed within the hub.

The opening of the second lumen is disposed in the end of the catheter tube where the end of the catheter tube is disposed within the hub. To axially space the opening of the first lumen from the opening of the second lumen within the hub, the opening of the first lumen may be formed as a cut in a portion of an outer wall of the first lumen. The cut may extend from the end of the catheter tube to axially space the opening of the first lumen from the opening of the second lumen. Alternatively, the opening of the first lumen may be a hole in the outer wall of the first lumen that is spaced from the end of the catheter tube. The outer wall may surround the first lumen and the second lumen and an inner wall may separate the first lumen from the second lumen.

The cut disposed in the outer wall of the first lumen may be formed so that a portion of the outer wall forms a sidewall having a height extending from the inner wall that separates the first lumen and the second lumen. In some configurations, the height of the sidewall may be less than or equal to about half a cross sectional length of the inner wall. Alternatively, the height of the sidewall may be the length of the portion of the outer wall that surrounds the first lumen or the height of the side wall is zero so that the side wall is flush with the inner wall and does not extend beyond the inner wall. In another configuration, a portion of the inner wall and the outer wall may be removed to axially space the opening of the first lumen from the opening of the second lumen.

The catheter may also include a first extension leg and a second extension leg attached to the hub. The first extension leg may be coupled to the first lumen for the delivery of fluids to the opening of the first lumen. Similarly, the second extension leg may be coupled to the second lumen for the delivery of fluids to the opening of the second lumen. Both the first extension leg and second extension leg may end in a luer fitting.

The catheter tube may also include a bend that is disposed within the hub. The opening of the first lumen and the opening of the second lumen may be disposed on opposite sides of the bend. The bend permits the first extension leg and the second extension leg to extend from the hub at an angle to each other. The angle may preferably range from about ten to about twenty degrees, but may also range from about five degrees to about ninety degrees.

A catheter of the invention may be made through the steps of obtaining a multiple lumen catheter tube, cutting the catheter tube to form an opening of the first lumen that is axially spaced with the opening of the second lumen, and attaching a hub to the catheter tube so that the opening of the first lumen and the opening of the second lumen are disposed within the hub. The method may also include the steps of bending the catheter tube so that the opening of the first lumen and the opening of the second lumen are disposed on opposite sides of the bend and disposing the bend within the hub. Additionally, the method may include the steps of inserting a first mandrel into the opening of the first lumen and inserting a second mandrel into the opening of the second lumen so that the first mandrel plugs the first lumen and second mandrel plugs the second lumen.

The method may also include the steps of removing the first mandrel from the first lumen and removing the second mandrel from the second lumen. The first mandrel may include a raised contact surface so that when the first mandrel is inserted into the opening of the first lumen, the raised contact surface abuts the inner wall of the catheter tube. The raised contact surface acts as a stop to prevent melted plastic during an injection molding process from cooling into a thin plastic flap between the inner wall and the mandrel. If a flap is formed, it may interfere with the use of the catheter and block the flow of fluid through the first lumen. Additionally, the bend in the catheter tube may be positioned proximate the raised contact surface during the injection molding process. The first mandrel may also include a bend which may be positioned proximate the raised contact surface.

Additionally the method may include the steps of attaching a first extension leg to the hub so that the first extension leg is coupled to the first lumen for the delivery of fluids to the opening of the first lumen and attaching a second extension leg to the hub so that the second extension leg is coupled to the second lumen for the delivery of fluids to the opening of the second lumen.

These and other features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
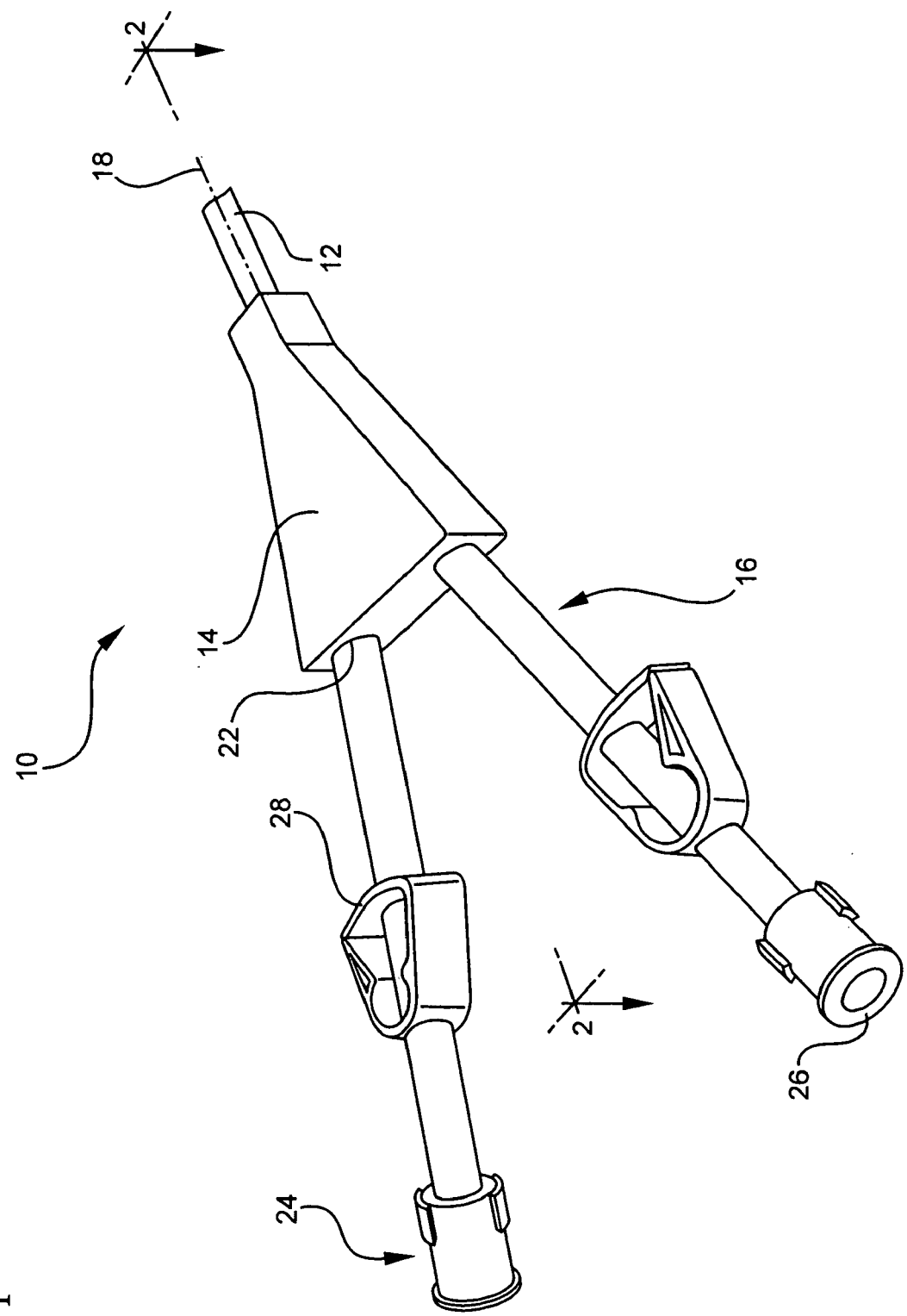
FIG. 1 is a perspective view of a catheter according to the invention.

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the catheter of the present invention, as represented in FIGS. 1 through 6, is not intended to limit the scope of the invention, as claimed, but is merely representative of presently preferred embodiments of the invention.

In accordance with the invention as embodied and broadly described herein in the preferred embodiment, a type of catheter is provided. More specifically, the catheter shown is a PICC 10. According to one embodiment, the PICC 10 may include a multiple lumen catheter tube 12, a hub 14, and extension legs 16. As shown, the multiple lumen catheter tube 12 includes a longitudinal axis 18 and is attached to the hub 14, which will be discussed below in greater detail with reference to FIG. 2.

Each extension leg 16 has a proximal end 22 that may be attached to the hub 14 and a distal end 24 that may include a luer fitting 26, known in the art. The extension legs 16 may be attached to the hub 14 by adhesives, mechanical means, such as a barbed or threaded coupling, or by molding the hub 14 over the proximal ends 22 of the extension legs 16. The extension legs 16 may also include leg clamps 28 that may be used to clamp off and prevent the flow of fluids through the PICC 10.

Figure 2:
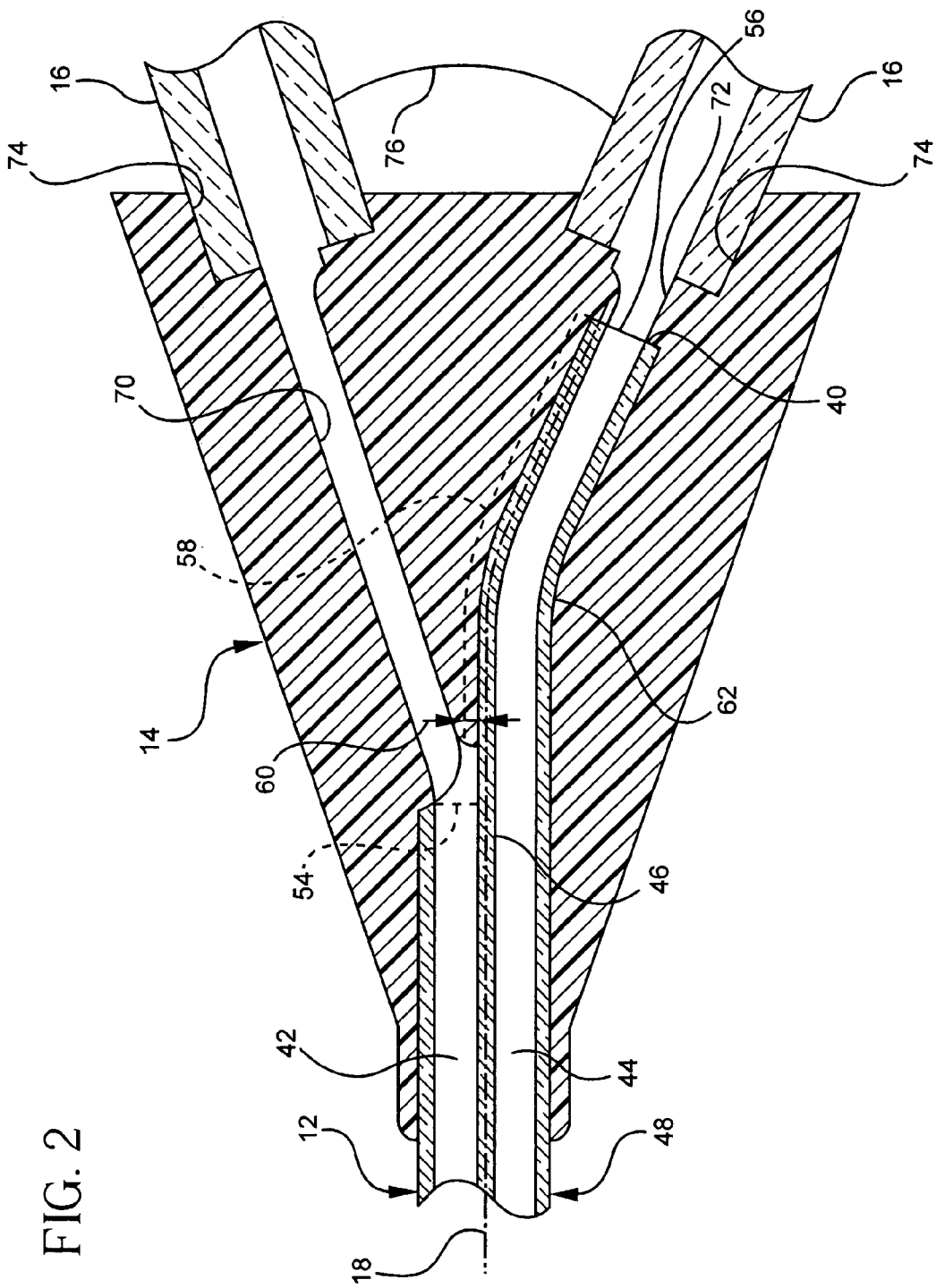
FIG. 2 is a cross sectional view of the catheter along line 2-2 of FIG. 1.

Referring to FIG. 2, a cross sectional view illustrates the PICC along line 2-2 of FIG. 1. As shown, an end 40 of the multiple lumen catheter tube 12 is disposed within the hub 14. The multiple lumen catheter tube 12 includes a first lumen 42 and a second lumen 44. Both the first lumen 42 and the second lumen 44 extend along the longitudinal axis 18. The first lumen 42 is separated from the second lumen 44 by an inner wall 46. The outer wall 48 is attached to the inner wall 46 and cooperates with the inner wall 46 to delineate the first lumen 42 and the second lumen 44.

The first lumen 42 opens in a first opening 54 and the second lumen 44 opens in a second opening 56, which are both positioned within the hub 14. The second opening 56 may be positioned at the end 40 of the multiple lumen catheter tube 12. The first opening 54 is spaced from the second opening 56 along the longitudinal axis 18. The first opening 54 is spaced from the second opening 56 in order to reduce the radial stress imposed on the multiple lumen catheter tube 12 during manufacture of the hub 14.

In forming the first opening 54, the outer wall 48 around the first lumen 42 may be cut so that a portion of the outer wall 48 proximate the first opening 54 forms a sidewall 58 having a height 60. The sidewall 58 provides additional surface area for thermal bonding between the multiple lumen catheter tube 12 and hub 14, as the hub 14 is molded over the multiple lumen catheter tube 12. Additionally in this configuration, the inner wall 46 is relatively unstressed and unaffected during manufacturing. Therefore, the inner wall 46 is better able to resist cross-lumen leakage even in high pressure applications above 100 psi.

The multiple lumen catheter tube 12 may also include a bend 62, which may be disposed within the hub 14. The bend 62 is a deviation in the multiple lumen catheter tube 12 from a straight line. The first opening 54 may be positioned on an opposite side of the bend 62 from the second opening 56. The bend 48 assists in positioning the first lumen 42 and the second lumen 44 to be in fluid communication with a respective extension leg 16. The bend 62 also helps to reduce the tendency of mandrels used to manufacture the hub 14 from stretching and stressing the multiple lumen catheter tube 12, which may lead to cross-lumen leakage while the PICC 10 is in use.

As shown, the hub 14 includes a first passage 70 and a second passage 72 that respectively couple the first lumen 42 and the second lumen 44 with the extension legs 16. The hub 14 also includes attachment features 74 for attaching the extension legs 16. The extension legs 16 may be attached to the hub 14 by an adhesive or a mechanical means, such as barbs or threads. Alternatively, the extension legs 16 may be attached as the hub 14 is molded. Of course, any combination of these methods may be used to attach the extension legs 16 and other methods may be used that are known by those of skill in the art.

The extension legs 16 may extend from the hub 14 at an angle 76 to each other. The angle 76 facilitates the separation of the distal ends 24 of the extension legs 16 from each other for convenience in the attachment of the PICC 10 to different sources of fluid to be administered to a patient. The angle 76 between the extension legs 16 may range from about five degrees to about ninety degrees, but preferably ranges between about ten degrees and about thirty degrees.

The multiple lumen catheter tube 12 may be made by extrusion and the hub 14 may be made by injection molding. Both the multiple lumen catheter tube 12 and the hub 14 may be made from plastic, such as a silicon polymer or polyurethane polymer, but preferably, the multiple lumen catheter tube 12 may be made from an alcohol resistant polyurethane, such as a polycarbonate polyurethane. The hub 14 may be made from the same plastic as the multiple lumen catheter tube 12, or the hub 14 may be made of a different plastic, such as polyether polyurethane. Typical site preparation for the insertion of the PICC 10 includes the use of an alcohol swab, thus, making the multiple lumen catheter tube 12 of an alcohol resistant polymer helps to prevent leakages that may result from weakening the outer wall of the multiple lumen catheter tube 12 through exposure to alcohol.

Referring to FIGS. 3A, 3B, 3C, and 3D, perspective views illustrate an end of a multiple lumen catheter tube 12 cut in different ways according to the invention for attachment to the hub 14 (shown in FIG. 2). As shown, the multiple lumen catheter tube 12 is generally circular in shape and the first lumen 42 and the second lumen 44 are generally D-shaped with generally equal cross sectional areas. The multiple lumen catheter tube 12 has an inner wall 46 attached to an outer wall 48 that cooperate to delineate the area of the first lumen 42 and the second lumen 44. Of course, a plurality of catheter tubes and lumens of other configurations can be used with the present invention and are within the scope of the present invention. For example, oval shaped catheters and catheters of other configurations having round lumens, oval lumens, square lumens, triangular lumens, and other types of lumens are also contemplated.

Figure 3B:
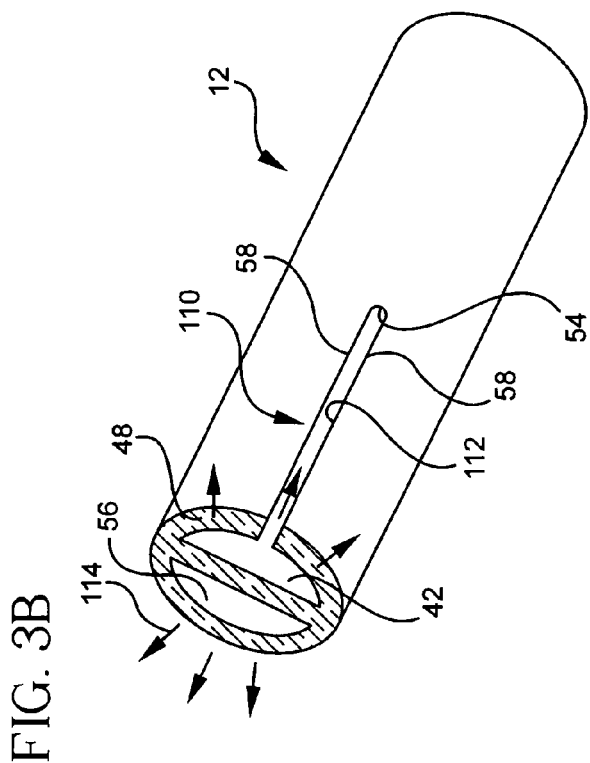
FIGS. 3A, 3B, 3C, and 3D are perspective views of an end of the multiple lumen catheter tube cut in different ways according to the invention for attachment to a hub.
Figure 3A:
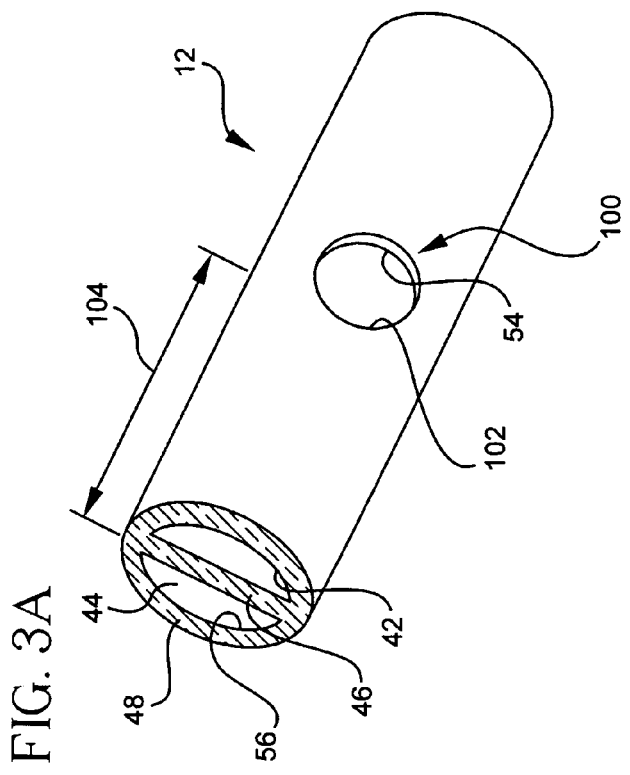

FIG. 3A illustrates a cut 100 that is a hole 102 in the outer wall 48 spaced from the end 40 of the multiple lumen catheter tube 12. The hole 102 permits a mandrel (shown in FIG. 4) to be inserted into and plug the first lumen 42. The portion 104 of the first lumen 42 between the end 40 and the hole 102 of the multiple lumen catheter tube 12 is filled during the formation of the hub 14 (shown in FIG. 2) to provide secure attachment between the hub 14 and the multiple lumen catheter tube 12 and to further prevent cross-lumen leakage.

FIG. 3B illustrates a cut 110 that is a slice 112 in the portion of the outer wall 48 that extends from the end 40 of the multiple lumen catheter tube 12 to the first opening 54 (shown in hidden lines). More specifically, as a mandrel (shown in FIG. 4) is inserted into the first lumen 42, the mandrel parts the outer wall 48 and extends through the slice 112. The outer wall 48 on either side of the slice 112 may form sidewalls 58. By spacing the first opening 54 from the second opening 56, the radial stresses 114 experienced by the multiple lumen catheter tube 12 during manufacturing are reduced.

The sidewall 58 may be trimmed to avoid the sidewall 58 from extending above the multiple lumen catheter tube 12 and contacting the mold (not shown) for forming the hub 14 as the hub 14 is formed. If the sidewall 58 contacts the mold (not shown), the sidewall 58 may be visible on the surface of the hub 14 and thus, may not be aesthetic.

Figure 3D:
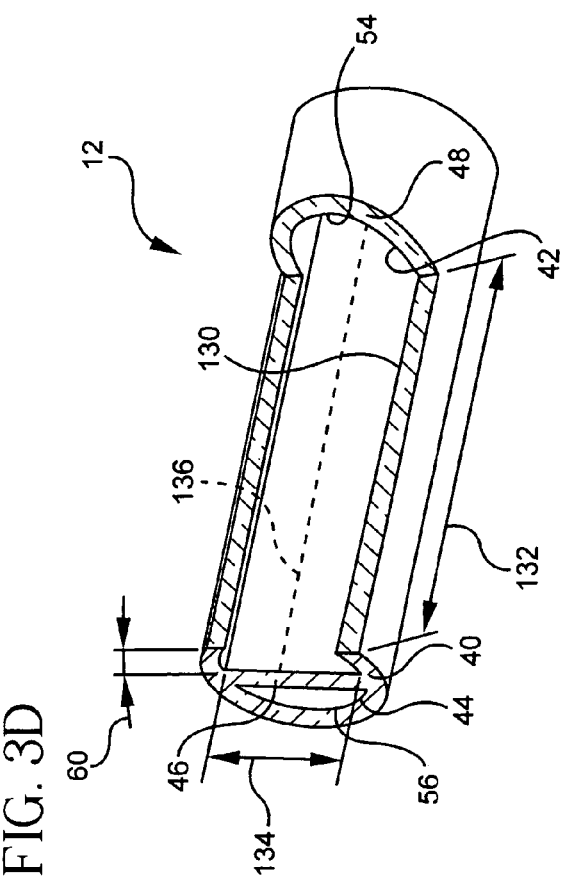
Figure 3C:
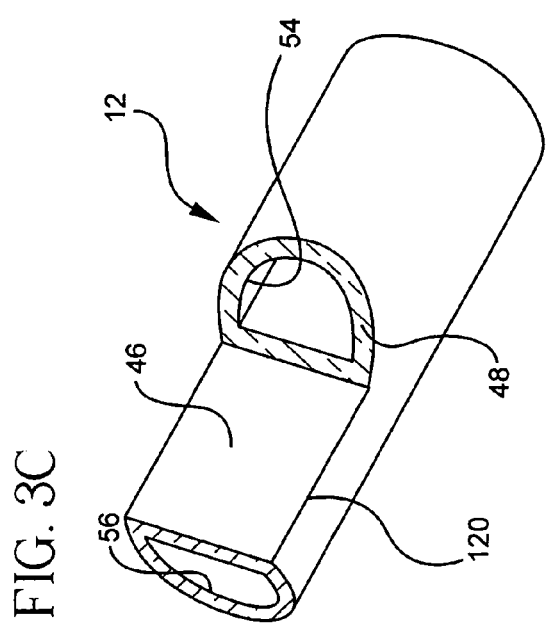

FIG. 3C illustrates a cut 120 where a portion of the inner wall 46 and the outer wall 48 have been removed in order to space the first opening 54 from the second opening 56. The cut 120 bisects the multiple lumen catheter tube 12 to reduce the axial stresses and stretching of the inner wall 46 and the outer wall 48 and permits the hub 14 (shown in FIG. 2) to help prevent cross lumen leakage.

FIG. 3D illustrates the end 40 of the multiple lumen catheter tube 12 as shown in FIG. 2. A cut 130 is positioned in the outer wall 48 so that a portion of the outer wall 48 forms the sidewall 58 having the height 60 that extends from the inner wall 46. The sidewall 58 provides additional surface area for bonding to the hub 14 (shown in FIG. 2). Additionally, the inner wall 46 remains uncut and unstressed to better resist cross lumen leakage.

The cut 130 may extend a distance 132 from the end 40 of the multiple lumen catheter tube 12. Alternatively, the cut 130 may be spaced from the end 40 similarly to the cut 100 shown in FIG. 3A. In some configurations, the distance 132 may extend from the end 40 and past the bend 62 (shown in FIG. 2) to better separate the first opening 54 from the second opening 56 within the hub 14 (shown in FIG. 2).

As shown in FIG. 3D, the inner wall 46 of the multiple lumen catheter tube 12 delineating the first lumen 42 has a cross sectional length 134 that may extend from the outer wall 48 to the outer wall 48. The height 60 of the sidewall 58 may range from zero to the fill length of the portion of the outer wall 48 used to delineate the first lumen 42. In some configurations of the invention, the height 60 of the sidewall 58 is less than or equal to about half the cross sectional length 134 of the inner wall 46. This configuration helps to prevent the sidewall 58 from protruding through the hub 14 (shown in FIG. 2), which may result in an unaesthetic catheter. Additionally, by limiting the height 60 of the sidewall 58 to less than or equal to about half the cross sectional length 134 of the inner wall 46, the sidewall 58 is not able to double over the center line 136 of the inner wall 46.

Figure 4:
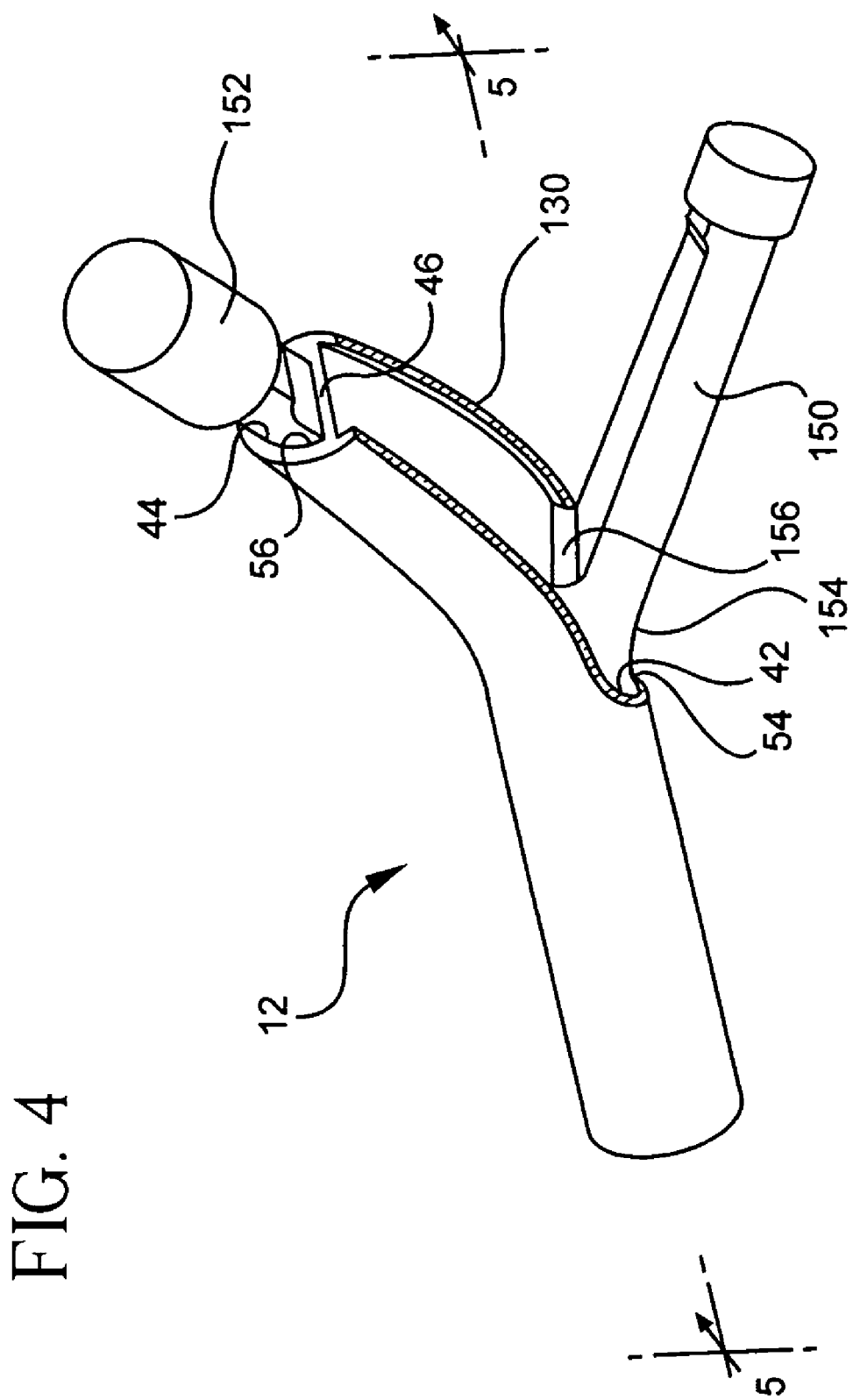
FIG. 4 is a perspective view of an end of the multiple lumen catheter tube and mandrels positioned in preparation for molding the hub.

Referring to FIG. 4, a perspective view illustrates the end 40 of a multiple lumen catheter tube 12 including the cut 130 with a first mandrel 150 and a second mandrel 152 positioned in preparation for molding the hub 14 (shown in FIG. 2). The first mandrel 150 extends through the first opening 54 into the first lumen 42 to plug the first lumen 42. Similarly, the second mandrel 152 extends through the second opening 56 into the second lumen 44 to plug the second lumen 44.

As shown, the first mandrel 150 may include a bend 154 and a raised contact surface 156 that abuts the inner wall 46 of the multiple lumen catheter tube 12. The bend 154 may be located near the raised contact surface 156 and the first opening 54 to facilitate positioning first mandrel 150 in the first lumen 42. The raised contact surface 156 may extend around the circumference of the first mandrel 150 or alternatively may only extend a distance similar to the cross sectional length 134 of the inner wall 46 of the multiple lumen catheter tube 12. The raised contact surface 156 may be located near the first opening 54 and is shaped to prevent plastic from forming a flap (not shown) between the first mandrel 150 during the molding of the hub 14 (shown in FIG. 2) and to be removed once the hub 14 is formed. The raised contact surface 156 may also be used to prevent the first mandrel 150 from being inserted too far within the first lumen 42 which can cause hoop stress on the multiple lumen catheter tube 12.

In some configurations, the first mandrel 150 and the second mandrel 152 may be a portion of the extension legs 16 (shown in FIG. 1). Thus, the first mandrel 150 and the second mandrel 152 are not removed, once the hub 14 (shown in FIG. 1) is formed. Additionally, the hub 14 is molded directly over the extension legs 16 and the multiple lumen catheter tube 12 in one step.

Figure 5:
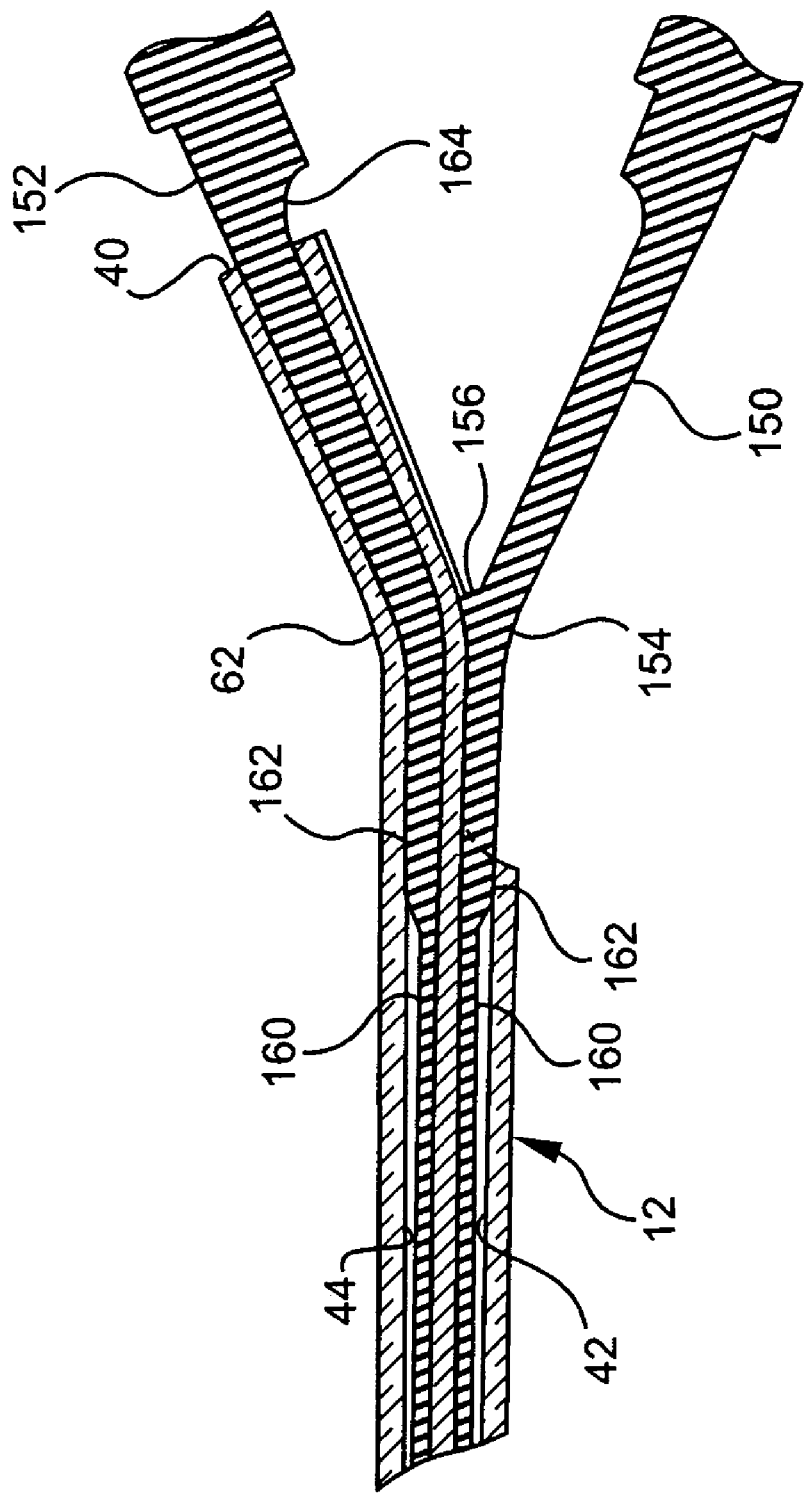
FIG. 5 is a cross sectional view along line 5-5 of FIG. 4 of the multiple lumen catheter tube and mandrels.

Referring to FIG. 5, a cross sectional view along line 5-5 of FIG. 4 illustrates the insertion of the first mandrel 150 and the second mandrel 152 within the multiple lumen catheter tube 12. Both the first mandrel 150 and the second mandrel 152 may include guide legs 160 that are narrower than the first lumen 42 and the second lumen 44 to facilitate the insertion of the first mandrel 150 and the second mandrel 152. The first mandrel 150 and the second mandrel 152 then widen from the guide legs 160 to the plug portions 162 which plug the first opening 54 and the second opening 56 of multiple lumen catheter tube 12.

Also illustrated, the bend 62 of the multiple lumen catheter tube 12 may be positioned near the bend 154 of the first mandrel 150. The second mandrel 152 may alternatively not include a bend by ending the guide leg 160 before the bend 62 of the multiple lumen catheter tube 12. The second mandrel 152 may also include a tube stop 164 that helps to prevent over insertion of the second mandrel 152.

The first mandrel 150 and the second mandrel 152 may be made of a flexible material, such as an elastomer having a higher melt temperature than the plastic of the hub 14 (shown in FIG. 2). A flexible material may facilitate removal of the first mandrel 150 and the second mandrel 152. Of course, the first mandrel 150 and the second mandrel 152 may be made of rigid materials such as ceramics, metal, composites, and rigid plastics.

Figure 6:
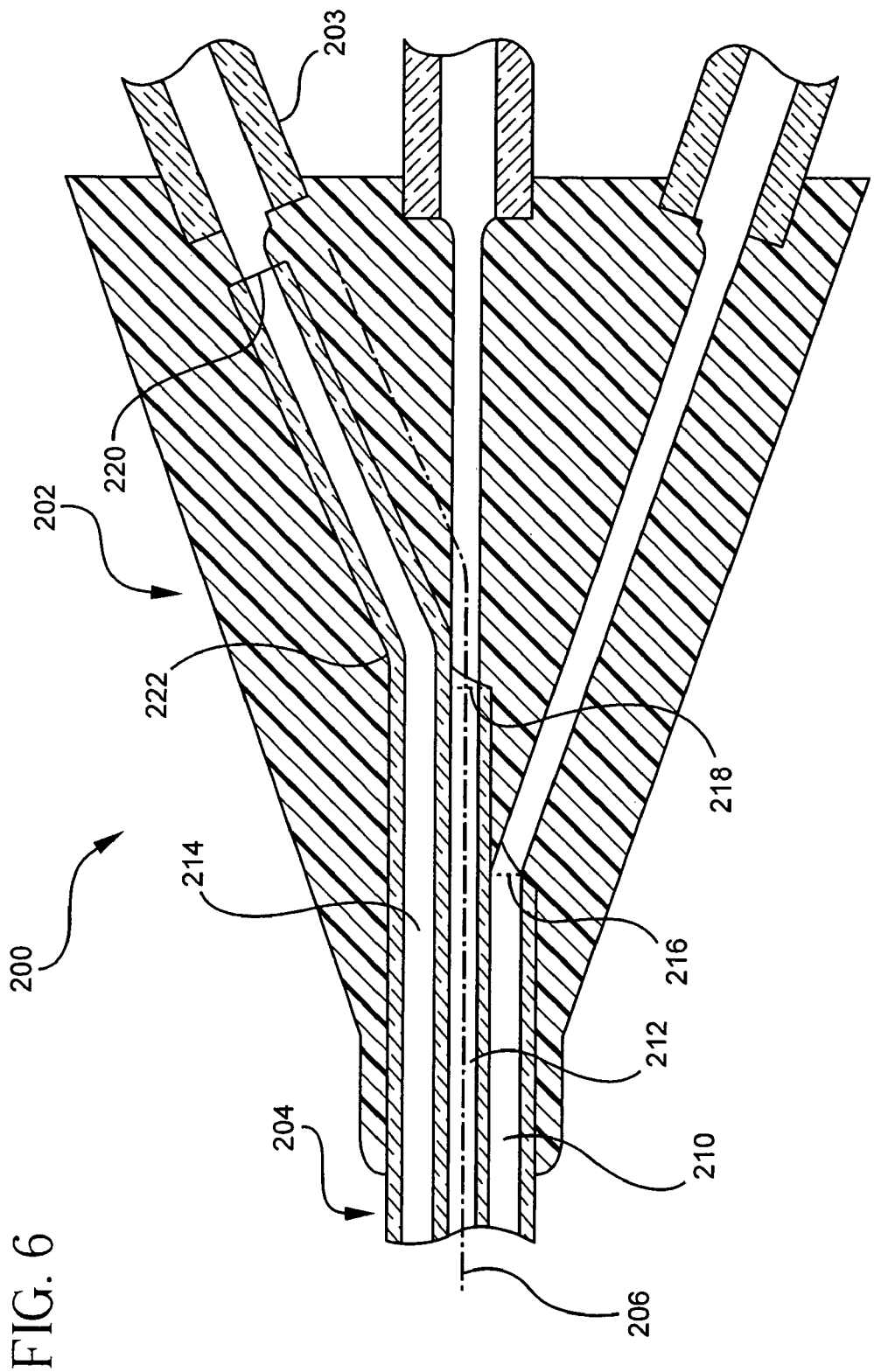
FIG. 6 is a plan view of another catheter according to the invention.

FIG. 6 is a plan view and illustrates another catheter 200 according to the invention. More specifically, FIG. 6 illustrates a hub 202 of the multiple lumen catheter 200 attached to extension legs 203 and a catheter tube 204 extending along a longitudinal axis 206 having a first lumen 210, a second lumen 212, and a third lumen 214.

The first lumen 210 has a first opening 216 and the second lumen 212 has a second opening 218. Additionally, the third lumen 214 has a third opening 220. The first opening 216, the second opening 218, and the third opening 220 may be spaced from each other along the longitudinal axis 206 to reduce the radial stresses that may be induced during manufacturing.

The catheter tube 204 may also include a bend 222 that may be positioned between the openings 216, 218, 220 along the longitudinal axis 206. For example, the bend 222 may be positioned between the second opening 218 and the third opening 220. The bend 222 helps to properly position the first opening 216, the second opening 218, and the third opening 220 so that they may each be placed in fluid communication with one of the extension legs 206. Of course, in some configurations of the invention, no bends may be used while in others, a plurality of bends may be used.

Figure 7:
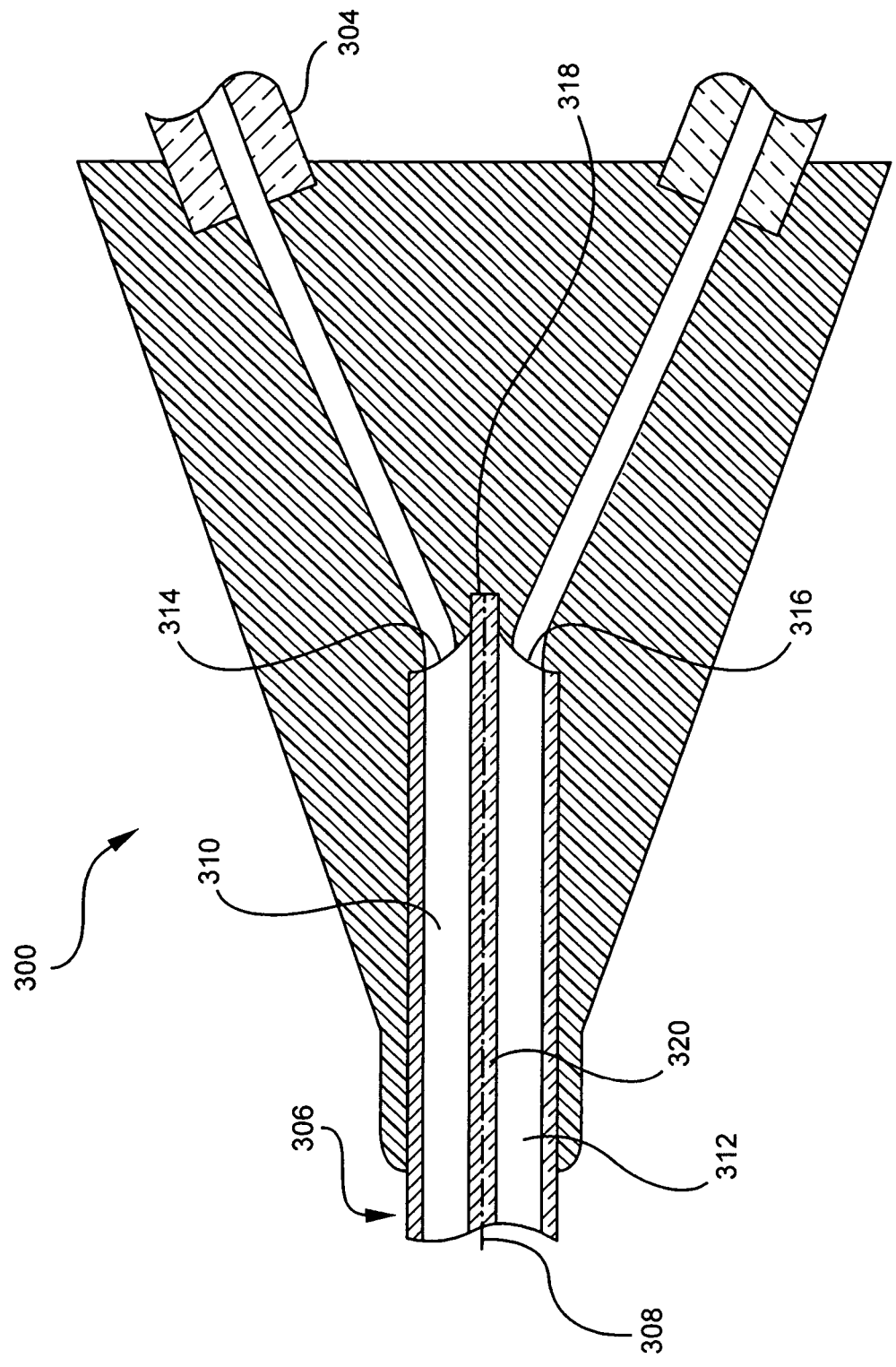
FIG. 7 is a plan view of an alternative catheter according to the invention.

FIG. 7 is a plan view and illustrates an alternative catheter 300 according to the invention. More specifically, FIG. 7 illustrates a hub 302 of the multiple lumen catheter 300 attached to extension legs 304 and a catheter tube 306 extending along a longitudinal axis 308 having a first lumen 310 and a second lumen 312.

The first lumen 310 has a first opening 314 and the second lumen 312 has a second opening 316. The first opening 314 and the second opening 316 may be about equally spaced from an end 318 of the catheter tube 306 along the longitudinal axis 308. The first opening 314 and the second opening 316 may be made in the catheter tube by any of the methods discussed above in relation to FIGS. 3A, 3B, 3C, and 3D.

By evenly spacing the first opening 314 and the second opening 316 from the end 318 of the catheter tube 306 within the hub 302, an inner wall 320 separating the first lumen 310 and the second lumen 312 remains uncut and unstressed to provide improved resistance to cross-lumen leakage. Additionally, the inner wall extending past the first opening 314 and the second opening 316 to the end 318 of the catheter tube 306 along the longitudinal axis 308 provides additional surface area for improved attachment of the hub 302 to the catheter tube 306.

Figure 8:
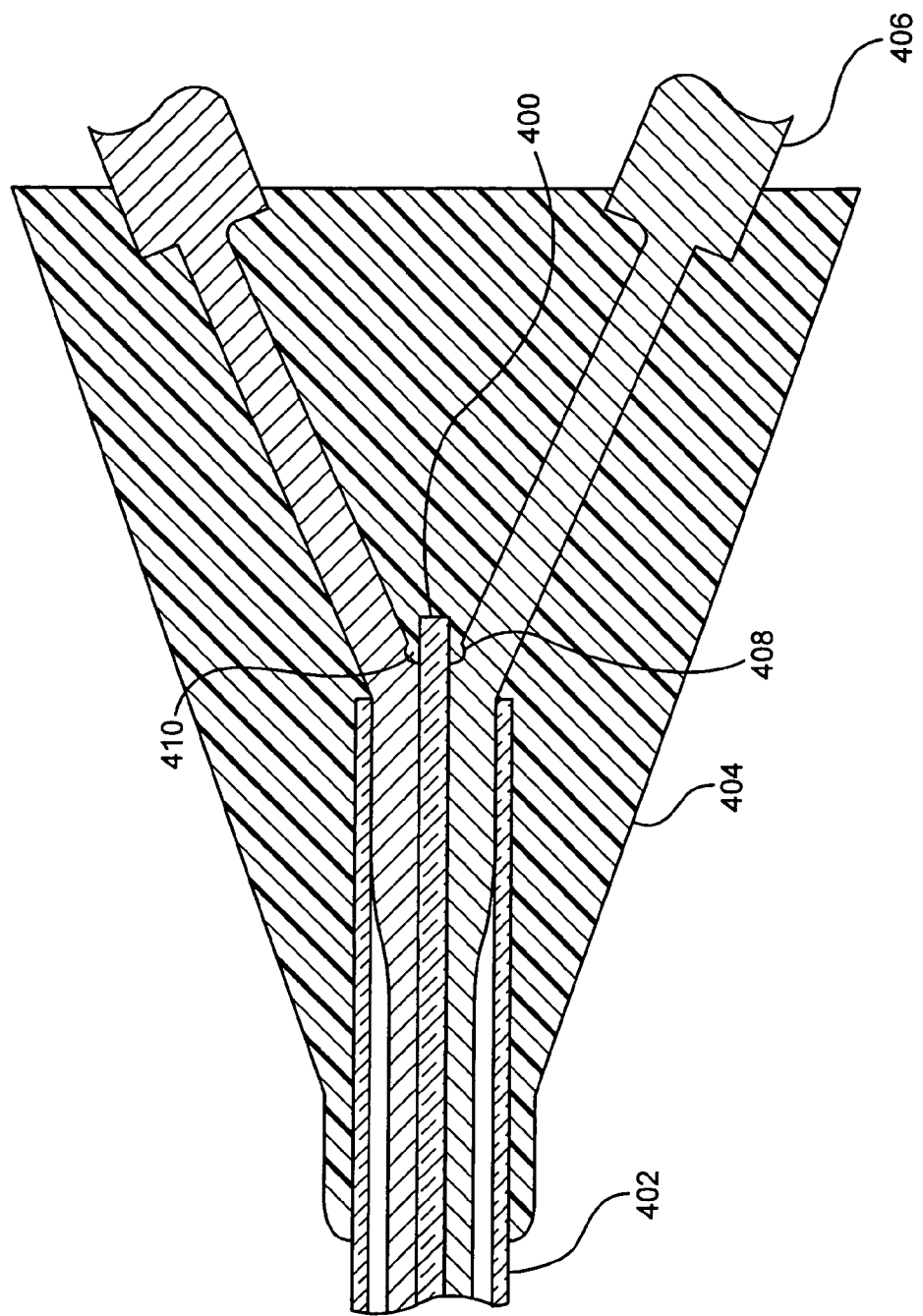
FIG. 8 is a plan view of another hub attached to a catheter tube according to the invention.

FIG. 8 is a plan view that shows an end 400 of a catheter tube 402 within a hub 404 with mandrels 406 positioned within the hub 404 and the end 400 of the catheter tube 402. The mandrels 406 include notches 408 that are located proximate the end 400 of the catheter tube 402. The notches 408 form a reinforced end joint 410 of the hub 404 when the hub 404 is molded over the end 400 of the catheter tube 402. The reinforced end joint 410 helps prevent the formation of flaps and to provide improved resistance to cross-lumen leakage. In other configurations, only one of the mandrels 406 may include a notch.

Thus, a catheter according to the invention may be used in high and low pressure applications to provide improved resistance to the formation of flaps and cross-lumen leakage. Additionally, a catheter according to the invention may be made entirely of plastic to facilitate recycling of the catheter. Of course, the catheter of the invention may also be made of metal, composites, ceramics and other materials known in the art.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter comprising:
a catheter tube having a longitudinal axis, a first lumen, and a second lumen wherein the first lumen and the second lumen extend through the catheter tube along the longitudinal axis, the first lumen and the second lumen each having an end, wherein the end of the first lumen is longitudinally spaced from the end of the second lumen; and
a hub attached to and enclosing at least a portion of the catheter tube, wherein the catheter tube has a bend disposed within the hub, and wherein the end of the first lumen and the end of the second lumen are disposed within the hub and on opposite sides of the bend along the longitudinal axis.

2. The catheter of claim 1, wherein hub comprises a reinforced end joint attached to the end of the catheter tube.

3. The catheter of claim 1, further comprising a first extension leg attached to the hub and coupled to the first lumen for the delivery of fluids to the opening of the first lumen and a second extension leg attached to the hub and coupled to the second lumen for the delivery of fluids to the end of the second lumen.

4. The catheter of claim 1, further comprising a hole through the outer wall into the first lumen wherein the hole is spaced from the end of the catheter tube.

5. The catheter of claim 1, wherein the first lumen and the second lumen are separated by an inner wall and surrounded by an outer wall, wherein a portion of the outer wall proximate the end of the first lumen forms a sidewall having a height.

6. The catheter of claim 5, wherein the height of the sidewall is less than or equal to about half the cross sectional length of the inner wall.

7. The catheter of claim 1, wherein the catheter tube comprises more than two lumens.

8. A catheter comprising:
a catheter tube having a longitudinal axis, a first lumen, and a second lumen, wherein the first lumen and the second lumen extend through the catheter tube along the longitudinal axis, the first lumen and the second lumen each having an opening, wherein the opening of the first lumen is longitudinally spaced from the opening of the second lumen; and
a hub attached to and enclosing at least a portion of the catheter tube, wherein the catheter tube has a bend disposed within the hub, wherein the openings of the first and second lumen are disposed within the hub and are longitudinally spaced on opposite sides of the bend.

9. The catheter of claim 8, further comprising a first extension leg attached to the hub and coupled to the first lumen for the delivery of fluids to the opening of the first lumen and a second extension leg attached to the hub and coupled to the second lumen for the delivery of fluids to the opening of the second lumen.

10. The catheter of claim 8, wherein the catheter tube has an end disposed within the hub and further comprising a hole through the outer wall and into the first lumen wherein the hole spaced from the end of the catheter tube.

11. The catheter of claim 8, wherein the first lumen and the second lumen are separated by an inner wall and surrounded by an outer wall, wherein a portion of the outer wall proximate the opening of the first lumen forms a sidewall having a height.

12. The catheter of claim 8, wherein the catheter tube comprises a bend disposed within the hub, wherein the opening of the first lumen and the opening of the second lumen are disposed on opposite sides of the bend.

13. A method for manufacturing a catheter, the method comprising:
cutting a sidewall of a catheter tube for preventing cross lumen leakage, the catheter tube comprising a longitudinal axis, an end, a first lumen, and a second lumen, wherein the first lumen and the second lumen extend through the catheter tube along the longitudinal axis, the first lumen and the second lumen each having an end, wherein the end of the second lumen is at the end of the catheter tube, wherein the step of cutting a sidewall of the catheter tube forms an end of the first lumen that is longitudinally spaced from the end of the catheter tube; and attaching a hub to and enclosing at least a portion of the catheter tube so that the end of the catheter tube, the end of the first lumen, and the end of the second lumen are disposed within the hub, and wherein the portion of the catheter tube disposed within the hub includes a bend and wherein the end of the first lumen and the end of the second lumen are longitudinally spaced from one another on opposite sides of the bend.

14. The method of claim 13, further comprising the step of bending the catheter tube so that the end of the first lumen and the end of the second lumen are disposed on opposite sides of the bend, wherein the bend is disposed within the hub.

15. The method of claim 13, further comprising the steps of inserting a first mandrel into the end of the first lumen and inserting a second mandrel into the end of the second lumen.

16. The method of claim 15, wherein inserting a first mandrel into the end of the first lumen and inserting a second mandrel into the end of the second lumen, the first mandrel plugs the first lumen and second mandrel plugs the second lumen.

17. The method of claim 15, further comprising the steps of removing the first mandrel from the first lumen and removing the second mandrel from the second lumen.

18. The method of claim 15, wherein the first mandrel comprises a raised contact surface, wherein inserting the first mandrel into the end of the first lumen, the raised contact surface abuts an inner wall of the catheter tube.

19. The method of claim 18, wherein the first mandrel comprises a bend disposed proximate the raised contact surface.

20. The method of claim 15, wherein one of the first mandrel and the second mandrel comprise a notch, wherein when the first mandrel is inserted into the end of the first lumen and the second mandrel is inserted into the end of the second lumen, the notch is disposed proximate the end of the catheter tube.

21. The method of claim 13, further comprising the steps of attaching a first extension leg to the hub so that the first extension leg is coupled to the first lumen for the delivery of fluids to the end of the first lumen and attaching a second extension leg to the hub so that the second extension leg is coupled to the second lumen for the delivery of fluids to the end of the second lumen.

22. The method of claim 13, wherein the catheter tube has an end disposed within the hub, wherein cutting the catheter tube, a cut is formed that extends from the end of the catheter tube.

23. The method of claim 13, wherein the catheter tube has an end disposed within the hub, wherein cutting the catheter tube, a hole is formed that is spaced from the end of the catheter tube.

24. The method of claim 13, wherein the first lumen and the second lumen are separated by an inner wall and surrounded by an outer wall, wherein cutting the catheter tube, a portion of the outer wall proximate the opening of the first lumen forms a sidewall having a height.

25. The method of claim 13, wherein the height of the sidewall is less than or equal to about half the cross sectional length of the inner wall.

26. A catheter comprising:
a hub;
a catheter tube disposed within the hub and having a bend disposed within the hub, the catheter tube having a longitudinal axis, an end, a first lumen, and a second lumen defined by an outer wall, wherein the first lumen and the second lumen extend through the catheter tube along the longitudinal axis, the first lumen and the second lumen each having an end, wherein the end of the first lumen is longitudinally spaced from the end of the second lumen and wherein the end of the first lumen and the end of the second lumen are longitudinally disposed on opposite sides of the bend.

* * * * *